United States Patent [19]
Finney

[11] 4,360,010
[45] Nov. 23, 1982

[54] PENILE PROSTHESIS

[75] Inventor: Roy P. Finney, Tampa, Fla.

[73] Assignee: Medical Engineering Corporation, Racine, Wis.

[21] Appl. No.: 244,335

[22] Filed: Mar. 17, 1981

Related U.S. Application Data

[63] Continuation-in-part of Ser. No. 150,231, May 15, 1980, Pat. No. 4,318,396.

[51] Int. Cl.³ .............................................. A61F 5/00
[52] U.S. Cl. .................................................... 128/79
[58] Field of Search ................. 128/79, DIG. 20; 3/1

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,066,073 | 1/1978 | Finney et al. | 128/79 |
| 4,187,839 | 2/1980 | Nuwayser et al. | 128/79 |
| 4,201,202 | 5/1980 | Finney et al. | 128/79 |
| 4,224,934 | 9/1980 | Scott et al. | 128/79 |
| 4,267,829 | 5/1981 | Burton et al. | 128/79 |

*Primary Examiner*—Stephen C. Pellegrino
*Attorney, Agent, or Firm*—Quarles & Brady

[57] ABSTRACT

A penile prosthesis includes at least one and preferably a pair of penile implants. The penile implant is a flexible, elongated member having a short proximal stem which is hollow and includes a fluid filled reservoir. The stem is adapted to be implanted into the root end of the corpus cavernosum to support the implant. The flexible member also includes an elongated flexible, non-distensible distal portion having a chamber substantially filled with a non-compressible fluid and a conical tip and an intermediate fluid filled pressure bulb pump which includes a valve mechanism. The valve mechanism allows fluid to be pumped from the reservoir in the stem into the non-distensible chamber to pressurize it and make it rigid. The implant includes a pressure relief valve which allows fluid to be transferred back to the reservoir.

5 Claims, 8 Drawing Figures

PENILE PROSTHESIS

RELATED APPLICATION

The present application is a continuation-in-part of my earlier patent application Ser. No. 150,231 filed on May 15, 1980, now U.S. Pat. No. 4,318,396 and titled "Penile Prostheses."

BACKGROUND OF THE INVENTION

The present invention relates to a penile prosthesis which is adapted to be implanted in man for treatment of erectile impotence.

There are instances of erectile impotence in which the patient does not respond to more conventional therapy and the surgical implanting of a penile prosthesis may be the only practical means of remedying the impotency.

Several types of penile prostheses have been employed in the past. One type of penile prosthesis is a pair of rods of suitable stiffness which are surgically implanted into the corpus cavernosum of the penis. One disadvantage of some of the rod-type implants is the permanent stiffness of the rod which can be a source of physical pain and/or embarrassment to the patient. The prostheses disclosed in U.S. Pat. No. 3,893,476 and U.S. Pat. No. 4,066,037 are representatives of the rod type prostheses.

Another type of penile prosthesis which is available is the inflatable prosthesis. The most common inflatable prosthesis includes two fairly long inflatable and distensible tubes that are surgically implanted in the corpus cavernosum of the penis. Each of the two tubes is connected by tubing to a pressure bulb of inflating fluid which is implanted elsewhere in the body. Because of the volume required to inflate, distend, pressurize and rigidize the inflatable tubes, the pressure bulbs are relatively large. The prostheses of U.S. Pat. No. 3,954,102 and U.S. Pat. No. 4,009,711 are representatives of the inflatable type prostheses.

SUMMARY OF THE INVENTION

It is the general object of the present invention to disclose a new type of penile prosthesis.

The penile prosthesis of the present invention comprises at least one and preferably a pair of penile implants. The implant is a flexible, elongated member having a short proximal stem which is hollow and includes a fluid filled reservoir, the stem is adapted to be implanted into the root end of the corpus cavernosum to support the implant. The flexible member also includes an elongated flexible, non-distensible distal portion having a chamber substantially filled with a non-compressible fluid and a conical tip and an intermediate fluid filled pressure bulb which includes a valve mechanism. The valve mechanism includes one way valves which allow fluid to be pumped from the pressure bulb and the reservoir in the stem into the non-distensible chamber in the distal portion of the implant and a pressure relief valve which allows fluid to be transferred back from the distal cylinder to the reservoir if the pressure in the distal cylinder exceeds a predetermined level. The distal portion of the implant is adapted to be implanted in the corpus cavernosum of the pendulus penis with the conical tip in the distal end of the corpus cavernosum.

In the preferred implant at least a portion of the wall of the hollow proximal stem is relatively stiff so that when it is implanted into the root end of the corpus cavernosum it will anchor and support the implant. The remainder of the stem wall and the shell of the pressure bulb are resilient so that they can be compressed to pump fluid through the one way valves to the non-distensible chamber in the distal portion and they will resume their normal non-compressed shapes when not being squeezed. The distal portion of the preferred implant contains a non-distensible chamber which is substantially filled with non-compressible fluid and is sufficiently flexible to allow the pendulus penis to assume a normal flaccid position when not pressurized and the tip of the distal portion of the preferred implant is paraboloidal in shape to fit the end of the corpus cavernosum, so as to enhance the physiological compatibility of the implant. Preferably, the entire implant, including the tip, is covered with a soft material so as to cause a minimum of irritation to the tissue of the penis.

Further objects and advantages of the prosthesis of the present invention will be come apparent from the drawings and the description of the preferred embodiment.

DESCRIPTION OF THE PREFERRED EMBODIMENTS

The preferred embodiment of the penile prosthesis of the present invention comprises a pair of elongated generally cylindrical implants which each include a fluid reservoir, a pressure pump and a non-distensible pressurizable chamber. The implants are identical, therefore, only one will be described in detail.

Figure 1:
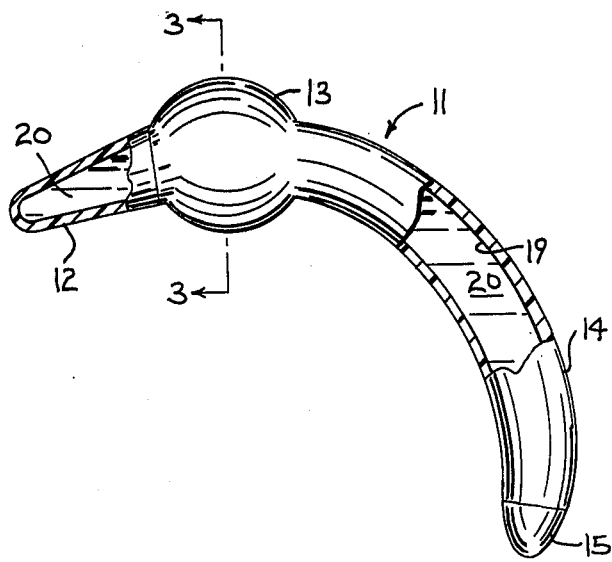
FIG. 1 is a side view, partly in section of the preferred embodiment of the penile implant of the present invention with the non-distensible chamber in a non-pressurized condition.
Figure 2:
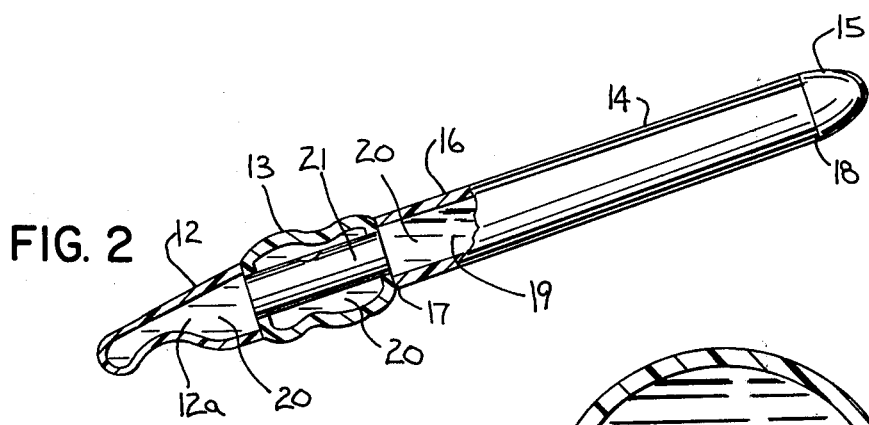
FIG. 2 is a side view similar to FIG. 1, with the non-distensible chamber of the implant pressurized.
Figure 3:
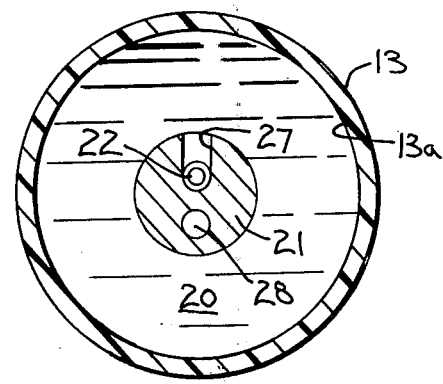
FIG. 3 is an enlarged cross sectional view taken along the line 3—3 of FIG. 1.

As seen in FIGS. 1 and 2, the implant 11 has a short hollow proximal stem 12 which is adapted to be implanted in the root end of the corpus cavernosum to support and anchor the implant, an intermediate pressure bulb 13, and a distal portion 14 including a conical tip 15. The distal portion 14 and the tip 15 are covered with a soft, flexible material and are adapted to be implanted into the corpus cavernosum of the pendulous penis. The tip 15 is paraboloidal in shape to conform to the inner shape of the end of the corpus cavernosum and preferably is made of a resealable material or includes a relatively thicker resealable outer layer which allows fluid to be injected or withdrawn by means of a fine hollow needle to regulate fluid volume after implantation.

As seen best in FIG. 2, the distal portion 14 of the implant 11 includes a tubular non-distensible sleeve 16, preferably of a silicone coated mesh or woven fabric, which is sealed at its ends 17 and 18 to the intermediate pressure bulb 13 and tip 15, respectively, in a fluid-tight manner to form a cylindrical non-distensible chamber 19. The seals 17, 18 may be made with a suitable adhesive or by other conventional means. As seen in FIG. 1, even in its non-pressurized state, the chamber 19 is substantially filled with a non-compressible fluid 20, such as saline or a free flowing silicone gel.

Referring specifically now to FIG. 1, it can be seen that when the non-distensible chamber 19 which contains the non-compressible fluid 20 is not pressurized, the soft, flexible, tubular distal portion 14 of the member 11 assumes a substantially flaccid position. However, when as seen in FIG. 2 the chamber 19 is completely filled and pressurized, the distal portion 14 is rigid. Thus the implant 11 if implanted can be used to cause the penis to assume a normal flaccid condition when not pressurized and an erectile position when pressurized.

Figure 4:
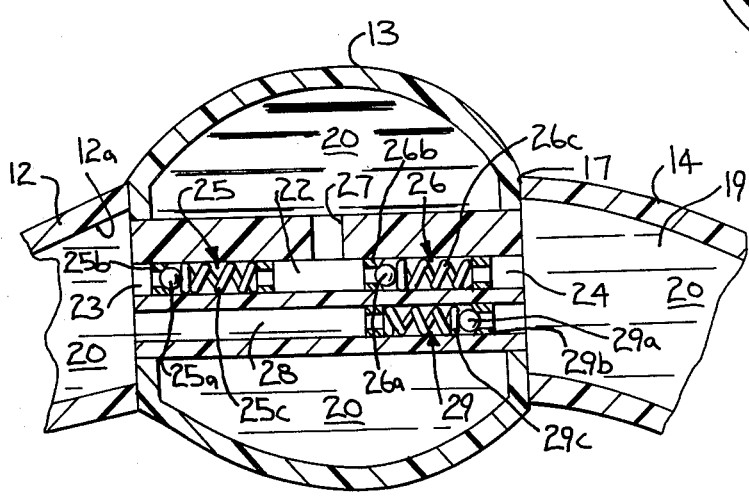
FIG. 4 is an enlarged side view, partially in section, of the pressure bulb and valve mechanism of the implant of FIG. 1.

As seen best in FIGS. 2 and 4, the stem 12 and distal portion 14 are separated by the pressure bulb 13 which serves as a pump to transfer fluid 20 from the reservoir 12a in the hollow stem 12 to the non-distensible chamber 19 in the distal portion 14.

Referring now specifically to FIGS. 2 to 6, it can be seen that the pressure bulb 13 includes a valve mechanism, generally referred to as 21. The valve mechanism 21 is generally cylindrical in shape and as seen best in FIGS. 4 to 6 it has a longitudinal passage 22 with an inlet 23 at one end which communicates with the reservoir 12a and an outlet 24 at the other end which leads to the chamber 19. The inlet is controlled by an inlet valve 25 and the outlet by an outlet valve 26. Intermediate the length of the passage 22 is a radial passage 27 which provides communication between the passage 22 and the interior 13a of the pressure bulb 13. The valve mechanism 21 also includes a pressure relief passage 28 and relief valve 29. The flow of the fluid between the reservoir 12a, pressure bulb 13 and chamber 19 is controlled by the valve mechanism 21.

As previously described, the non-distensible chamber 19 of the implant 11 is completely filled and pressurized by manually squeezing and compressing the wall of the pressure bulb 13 so as to pump fluid 20 under pressure from the pressure bulb 13 and the fluid filled hollow reservoir 12a into the already substantially filled chamber 19 to completely fill and pressurize it and make it rigid.

The operation of the valve mechanism 21 now will be described in detail.

Figure 5:
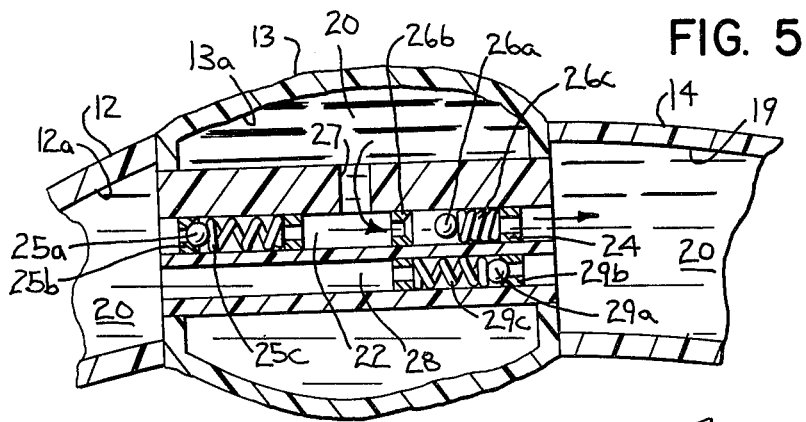
FIG. 5 is a view similar to FIG. 4 in which the pressure bulb is partially compressed.
Figure 6:
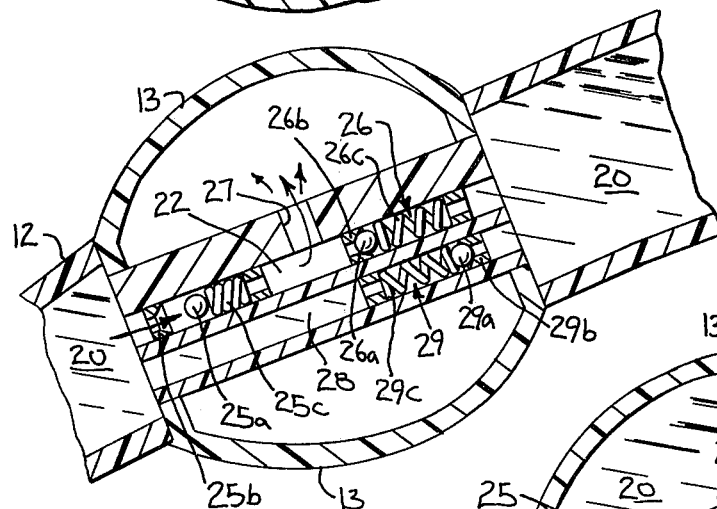
FIG. 6 is a view similar to FIG. 4 in which the pressure bulb has resumed its original shape after having been completely compressed.

As seen in FIG. 4, the inlet valve 25 which includes a ball 25a, a valve seat 25b, and a calibrated spring 25c, and the outlet valve 26 which also includes a ball 26a, a seat 26b and a spring 26c are closed. When the pressure bulb 13 is partially squeezed, as seen in FIG. 5, fluid pressure on the ball 25a forces it onto its seat 25b keeping the inlet valve 25 closed and preventing fluid in the pressure bulb 13 from flowing to the reservoir 12a, however, the fluid pressure on the ball 26a moves it off its seat 26b so that the outlet valve 26 opens. The opening of valve 26 allows the transfer of fluid 20 from the interior 13a of the bulb 13 to the chamber 19 via the passages 27 and 22 and the outlet 24. As seen in FIG. 6, upon release of a compressive force on the pressure bulb 13, the resilient wall of the bulb 13 resumes its normal bulbar shape creating a negative pressure within the bulb 13. As a result, the fluid pressure exerted on the ball 25a by the fluid 20 in the reservoir 12a exceeds the force of the spring 25c and it causes the ball 25a to move off its seat 25b and to allow the interior 13a of the bulb 13 to refill with fluid 20 from the reservoir 12a. Thus, when the bulb 13 is once again squeezed the fluid 20 originally in the reservoir 12a is pumped into the non-distensible chamber 19 causing it to become rigid. The valve mechanism 21 also includes the calibrated pressure relief valve 29 which opens to allow the transfer of fluid 20 back to the reservoir 12a via the relief passage 28 whenever a predetermined safe pressure in the chamber 19 is exceeded.

During the pressurization operation, the pressure relief valve 29 of the valve mechanism 21 remains closed. More specifically, the ball 29a of the relief valve 29 is kept by the force of the spring 29c upon its seat 29b so that the fluid which has entered the non-distensible chamber 19 under pressure cannot escape therefrom. However, when the pressure in the chamber 19 exceeds the force of the spring 29c or it is desired to depressurize the chamber 19, fluid 20 can be transferred back to the reservoir 12a in the stem 12 by opening the relief valve 29. This is readily accomplished by the user squeezing the penis in which the implant 11 is implanted so as to cause the pressure in the chamber 19 to exceed the force of the spring 29c and to move the ball 29a off its seat 29b which opens the valve 29 and permits fluid 20 to return to the reservoir 12a via the passage 28. As a safety feature, the valve 29 automatically opens whenever the pressure in the non-distensible chamber 19 exceeds the predetermined pressure required for an erection. Such excess pressure within the non-distensible chamber 19 can be the result of over-pumping or as a result of the penis being accidentally bent or otherwise compressed. The pressure relief valve 29 serves not only as a means for depressurizing the chamber 19 when an erection is no longer desired, but it also serves as a safety valve to prevent over-pressures in the chamber. In addition, when a pair of implants are implanted, the implants selected will preferably have pressure relief valves which open at the same predetermined pressure which permits the user to automatically equate the pressure in the non-distensible chambers of each of the implants.

The unique construction of the preferred penile implant 11 which includes the tubular non-distensible chamber 19, which is in the non-pressurized state substantially filled with non-compressible fluid 20, the stem reservoir 12a, the pressure bulb 13 and the valve mechanism 21 eliminates the need for the separate pressure bulbs of the prior art pressurizable penile prostheses.

Figure 7:
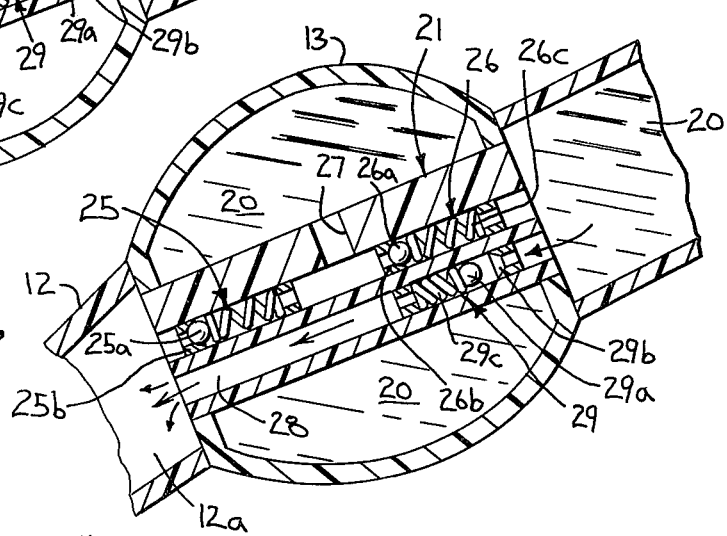
FIG. 7 is a view similar to FIG. 4 in which the pressure relief valve is open.
Figure 8:
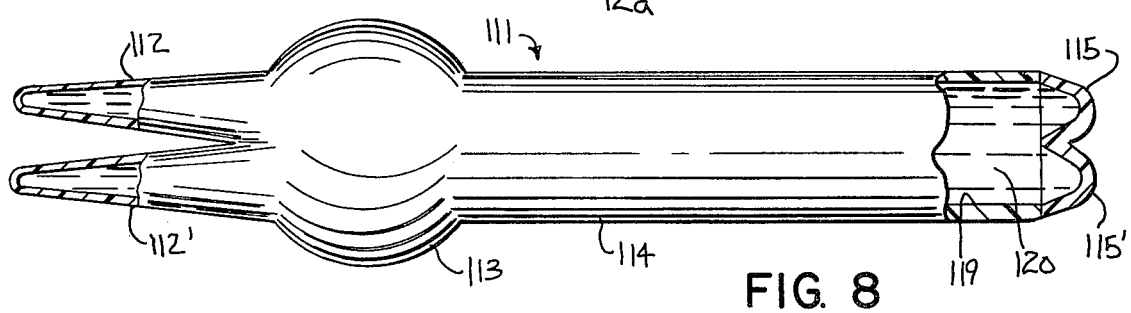
FIG. 8 is a top view partly in section of a second embodiment of the implant of the present invention.

A second embodiment of the invention which might be preferred for some uses is shown in FIG. 7. As seen therein, an implant 111 comprises a unitary member having a pair of hollow proximal stems 112, 112[1] at the distal end, a single intermediate pressure bulb 113 and a common distal portion 114 with a pair of tips 115, 115[1]. The pressure bulb 113 includes a single valve mechanism (not seen) similar to that previously described for transferring the fluid 120 under pressure from the reservoirs 112a and 112a to the chamber 119 to fill and pressurize it and make it rigid.

The novel implant of the preferred embodiment of the present invention, in addition to being unique in design, differs from prior art inflatable implants in that the wall of the pressurizable chambers are non-distensible, i.e., it does not stretch or inflate. Another important difference is that the chamber in the distal portion of the implant even in a non-pressurized state is substantially filled with a non-compressible fluid so that only a relatively small amount of fluid is required to fill and pressurize the chamber to make the distal portion of the implant rigid.

The term "substantially filled" as used herein to describe the fluid content of a chamber means that the chamber contains about 60% to about 95% or more, but less than 100% of its capacity of a non-compressible fluid such as water, saline or a free flowing gel. The actual content of fluid can vary; however, the distal portion of the implant when "substantially filled" should be still sufficiently non-rigid and flexible so that the penis can assume a normal flaccid position.

All the parts and components of the prosthesis are preferably made of or are covered with a medical grade silicone rubber which is soft, non-reactive, non-toxic and well tolerated by the adjacent organic tissues. Silicone rubber is preferred because it is quite resistant to wear and tear and remains functional for long periods of time. However, other suitable materials possessing desirable properties also can be employed.

The sleeve which forms the wall of the chamber of the preferred implant is made of a mesh or fabric covered with silicone material so that it will not stretch or distend when filled with fluid and excessive pressure will not be exerted on the tunica albuginea. The diameter of the sleeve is selected so that it will fill the corpus cavernosum when the implant is in its non-pressurized state.

The hollow proximal stem of the preferred implant will have at a least a portion of its wall formed of a relatively stiff material to anchor and support the erect implant. The anchoring portion of the stem wall may have a Shore A hardness of about 70, and the remainder of the stem wall and the distal tips a Shore A hardness of about 20. Each of the materials has sufficient tensile strength for its intended use.

The preferred method of implantation of the implants is through incisions made at the penoscrotal junction and in the penis. After appropriate incisions, the corpora cavernosum are dilated distally and proximally to accept the implants. In selecting the proper size implant, anatomical measurements are first made to insure that the proximal stem of the implant will be positioned at the base of the penis below the pelvic bone and the pressure bulb will be at the penile shaft. An implant having the appropriate sized stem and distal portion and tip is selected. The distal portions are then inserted into the corpora cavernosum of the penis. The distal tips are positioned in the tunica ends of the corpora cavernosum and the proximal stems are anchored in the root ends. The proximal stems of the two implants preferably will diverge laterally to accomodate the anatomy and provide lateral stability to the penis. The incisions are then closed.

Once a pair of the preferred implants have been implanted as described, and the reservoirs, the pressure bulbs and the non-distensible chambers of the implants are substantially filled with a non-compressible fluid, the user can by squeezing the pressure bulb through the skin pressurize the chambers of the implants to effect an erection. As previously described, squeezing the pressure bulb pumps the fluid from the reservoir in the stem and the fluid already within the bulb through the valve mechanism and into the non-distensible chamber.

It will be appreciated that by the repeated compressing and relaxing of the bulbs, the user forcibly pumps the non-compressible fluid into the non-distensible chambers of the implanted implants under pressure. The successive repeated squeezing of the bulbs incrementally increases the pressure within the non-distensible chambers to completely fill and expand the chambers, causing the chambers and the penis to become rigid.

In addition to the spring and ball type valves shown in the drawing, it will be apparent to those skilled in the art that other types of pressure sensitive valves which can be calibrated could be used such as magnetic valves and the like. In addition, the entire valve mechanism 21 including the valves could be made of silicone elastomer. Generally, any valve which will be normally closed but will open when the fluid pressure exceeds a predetermined value is potentially useful. For example, if 300 millimeters of Hg pressure is needed to make the non-distensible chamber rigid and the bursting pressure of the chamber is 400 millimeters of Hg, then the valve selected as a relief valve should be one that will open at something less than 400 millimeters Hg, and preferably at 300 millimeters of Hg.

It will also be apparent to those skilled in the art that a number of other modifications and changes can be made without departing from the spirit and scope of the present invention. Therefore, it is to be understood that invention is not to be limited except by the claims which follow.

I claim:

1. A penile implant comprising a flexible, elongated member having a relatively short, hollow, proximal stem, said stem having a wall portion which is relatively stiff so as to support and anchor the implant and a reservoir for inflating fluid; an elongated flexible distal portion having a non-distensible, pressurizable chamber and a tip and pump means located within said elongated member between the reservoir in the hollow stem and the pressurizable chamber for transferring fluid from the reservoir to the non-distensible chamber.

2. The penile implant of claim 1 in which the pump means is a pressure bulb.

3. The penile implant of claim 1 in which the pump means includes valve means which allow fluid to be transferred from the reservoir to the pump and from there to the pressurizable chamber.

4. The penile implant of claim 3 in which the valve means includes a pressure relief valve which prevents the pressurizable chamber from being over-pressurized.

5. The penile implant of claim 3 in which the pump means is a pressure bulb and the valve means is located within the pressure bulb.

* * * * *